US00PP33024P2

(12) United States Plant Patent
O'Connell

(10) Patent No.: US PP33,024 P2
(45) Date of Patent: May 4, 2021

(54) ***KALANCHOE* PLANT NAMED 'FIRE RAINBOW'**

(50) Latin Name: *Kalanchoe sexangulare*
Varietal Denomination: FIRE RAINBOW

(71) Applicant: Altman Specialty Plants, Inc, Vista, CA (US)

(72) Inventor: Renee O'Connell, Escondido, CA (US)

(73) Assignee: Altman Specialty Plants, Inc, Vista, CA (US)

( * ) Notice: Subject to any disclaimer, the term of this patent is extended or adjusted under 35 U.S.C. 154(b) by 0 days.

(21) Appl. No.: 16/873,316

(22) Filed: Mar. 17, 2020

(51) Int. Cl.
*A01H 5/02* (2018.01)
*A01H 6/32* (2018.01)

(52) U.S. Cl.
USPC ..... Plt./335

(58) Field of Classification Search
USPC ..... Plt./335
CPC ..... A01H 5/02
See application file for complete search history.

*Primary Examiner* — Kent L Bell
(74) *Attorney, Agent, or Firm* — Cassandra Bright

(57) ABSTRACT

A new and distinct cultivar of *Kalanchoe* plant named 'Fire Rainbow' is disclosed, characterized by rosettes of green leaves with margins of lemon yellow, blushing rose red in bright light and cooler temperature. The new cultivar freely branches, enabling increased and faster propagation. The new cultivar 'Fire Rainbow' exhibits robust and rapid growth. The freely branching characteristic exhibited by the new cultivar, in combination with the robust, moderately rapid growth of the new cultivar 'Fire Rainbow', results in attractive clustering brightly colored variegation, useful for decorative combinations for special occasions or for container gardens on the patio.

1 Drawing Sheet

Latin name of the genus and species: *Kalanchoe sexangulare.*

Variety denomination: 'FIRE RAINBOW'.

BACKGROUND OF THE INVENTION

The new cultivar is the result of a naturally-occurring mutation. The new cultivar 'Fire Rainbow' was discovered by the inventor, Renee O' Connell as a whole plant mutation in March 2016 at a commercial greenhouse in Vista, Calif., among a population of unnamed *Kalanchoe sexangulare* plants.

Asexual reproduction of the new cultivar 'Fire Rainbow' was first performed in Vista, Calif., at a commercial greenhouse, by terminal vegetative cuttings in May of 2016. *Kalanchoe* 'Fire Rainbow' has since produced multiple generations and has shown that the unique features of this cultivar are stable and reproduced true to type.

SUMMARY OF THE INVENTION

The cultivar 'Fire Rainbow' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'FIRE RAINBOW'. These characteristics in combination distinguish 'FIRE RAINBOW' as a new and distinct *Kalanchoe* cultivar:

CPC ..... *A01H 6/324* (2018.05)

1. *Kalanchoe sexangulare* 'Fire Rainbow' produces rosettes of green leaves with margins of lemon yellow, blushing rose red in bright light and cooler temperatures.

2. *Kalanchoe sexangulare* 'Fire Rainbow' displays a fast growth rate as compared to many other *Kalanchoes.*
3. *Kalanchoe sexangulare* 'Fire Rainbow' branches freely to produce an attractive cluster of brightly colored variegation, useful for decorative combinations for special occasions or for container gardens on the patio.

PARENTAL COMPARISON

Plants of the new cultivar are similar to plants of the parent in, most horticultural characteristics, however, plants of the new cultivar differ in the following;

1. *Kalanchoe sexangulare* 'Fire Rainbow' produces leaves of green with margins of lemon yellow, blushed rose red in bright light and cooler temperatures, the parent variety produces green leaves that blush deep red when stressed by high light or cold.

As this is a mutation, there is no pollen parent.

COMMERCIAL COMPARISON

The new cultivar 'Fire Rainbow' can be compared to the unpatented, unnamed variety of *Kalanchoe luciae* available commercially. Plants of the unnamed *Kalanchoe luciae* available commercially are similar to plants of the new cultivar 'Fire Rainbow' in most horticultural characteristics. However, the new cultivar 'Fire Rainbow' differs in the following:

1. *Kalanchoe sexangulare* 'Fire Rainbow' produces green leaves with margins of lemon yellow, blushed rose red in bright light and cooler temperatures, whereas this comparator produces milky green leaves that blush rose in cooler temperatures or in high light.
2. *Kalanchoe sexangulare* 'Fire Rainbow' is a branching, upright growing plant, whereas this comparator forms more compact, rosettes of lower morphology.
3. *Kalanchoe sexangulare* 'Fire Rainbow' produces longer leaves, with margins having irregularly shaped, somewhat shallow crenations, whereas this comparator produces more rounded leaves with entire margins.

The new cultivar 'Fire Rainbow' can be compared to the unpatented, unnamed variety *Kalanchoe orgyalis*, widely available commercially. Plants of the commercial, unnamed *Kalanchoe orgyalis* are similar to plants of the new cultivar 'Fire Rainbow' in most horticultural characteristics. However, the new cultivar 'Fire Rainbow' differs in the following:

1. *Kalanchoe sexangulare* 'Fire Rainbow' produces green leaves with margins of lemon yellow, blushed rose red in bright light and cooler temperatures, whereas this comparator produces dull green leaves covered with a copper felty texture.
2. *Kalanchoe sexangulare* 'Fire Rainbow' has leaves with margins having irregularly shaped, somewhat shallow crenations, whereas this comparator produces ovate spatulate leaves with entire margins.
3. *Kalanchoe sexangulare* 'Fire Rainbow' exhibits a faster growth rate than this comparator.

BRIEF DESCRIPTION OF THE PHOTOGRAPH

The accompanying photograph illustrates in full color a typical plants of 'FIRE RAINBOW' grown in a greenhouse in Vista, Calif. (approximately 3000 foot candles). The photograph was taken using conventional techniques and equipment. While the colors in this photograph may display variances of color as compared to the living cultivar, due to LRV (light reflectance value), it is as accurate as possible using conventional photographic techniques. Colors in the photograph may appear to differ slightly from the color values cited in the botanical description, which accurately describe the colors of the new *Kalanchoe* plant. Temperatures ranged from about −1° C. to 29° C. night and day. No artificial light, photoperiodic treatments or chemical treatments were given to the plants.

DETAILED BOTANICAL DESCRIPTION

In the following description, color references are made to R.H.S. Colour Chart, 2007, except where general terms of ordinary dictionary significance are used. The following observations and measurements describe *Kalanchoe sexangulare* 'Fire Rainbow' plants in a commercial greenhouse in Vista, Calif., Temperatures ranged from −1° C. to 29° C. night and day. No artificial light, photoperiodic treatments or chemical treatments were given to the plants. Natural light conditions were approximately 2500 to 4000 fc of light. Measurements and numerical values represent averages of typical plant types.

Botanical classification: *Kalanchoe sexangulare* 'Fire Rainbow'.

PROPAGATION

Type of propagation typically used: Terminal vegetative cuttings.
Time to initiate roots: About 10 days at approximately 24° C.
Root description: Fibrous.

PLANT

Age of plant described: Approximately 4 months from a cutting.
Container size of the plant described: 1 gallon.
Growth habit: Upright branching sub-shrub.
Height: Approximately 15 cm to top of highest leaf.
Plant spread: Approximately 28 cm. Plant comprised of 3 to 6 main stems.
Growth rate: Moderately fast.
Branching characteristics: Freely branching from an early age. Approximately 3 to 6 primary branches from the center of the plant.
Length: Average 4 to 8 cm.
Diameter: Average range 4 to 7 mm.
Strength: Moderate.
Color: Near RHS Greyed-Red 181B.
Texture: Glabrous.
Internode: Average range 8 mm to 24 mm.

FOLIAGE

Leaf:
- *Arrangement*.—Opposite.
- *Average length*.—Approximately 8 to 11 cm.
- *Average width*.—5.0 cm, naturally folded.
- *Width at base*.—8 mm.
- *Shape of blade*.—Oblate.
- *Apex*.—Rounded obtuse.
- *Base*.—Attenuate.
- *Margin*.—Irregularly shaped somewhat shallow crenations.
- *Texture of top surface*.—Glabrous.
- *Texture of bottom surface*.—Glabrous.
- *Quantity*.—Approximately 8 to 12 per stem.
- *Aspect*.—Strongly folded upward. Cannot be unfolded without breaking leaf.
- *Color*.—Young foliage, upper side: Near RHS Green 138B. Thick margin Yellow 10D flushed Red 52B. Young foliage, under side: Near RHS Green 138B. Thick margin Yellow 10D flushed Red 52B. Mature foliage upper side: Near RHS Green 138B. Margin Yellow 10D heavily flushed Red 52B. Mature foliage, under side: Near RHS Green 138B. Margin Yellow 10D heavily flushed Red 52B.
- *Venation*.—There is no visual appearance of venation. Indistinguishable from leaf blade.

Petiole:
- *Length*.—Young foliage near 2 cm; mature foliage near 4 cm.
- *Width*.—Approximately 0.8 cm.
- *Texture*.—Glabrous.
- *Color*.—Interior near Green 138B, Outer section near Yellow 10D.

FLOWER

Not observed.

REPRODUCTIVE ORGANS

Not observed.

OTHER CHARACTERISTICS

Fruits and seeds: Not observed to date.

Temperature tolerance: Tolerates temperatures from approximately 0° C. to at least 32° C.

Disease/pest resistance: Some resistance to powdery mildew. Neither resistance or susceptibility to other normal diseases and pests of *Kalanchoe* has been observed.

Drought tolerance: Tolerates at least 3 weeks of high temperatures without supplemental water, showing no serious damage to plant.

What is claimed is:

1. A new and distinct cultivar of *Kalanchoe* plant named 'FIRE RAINBOW' as herein illustrated and described.

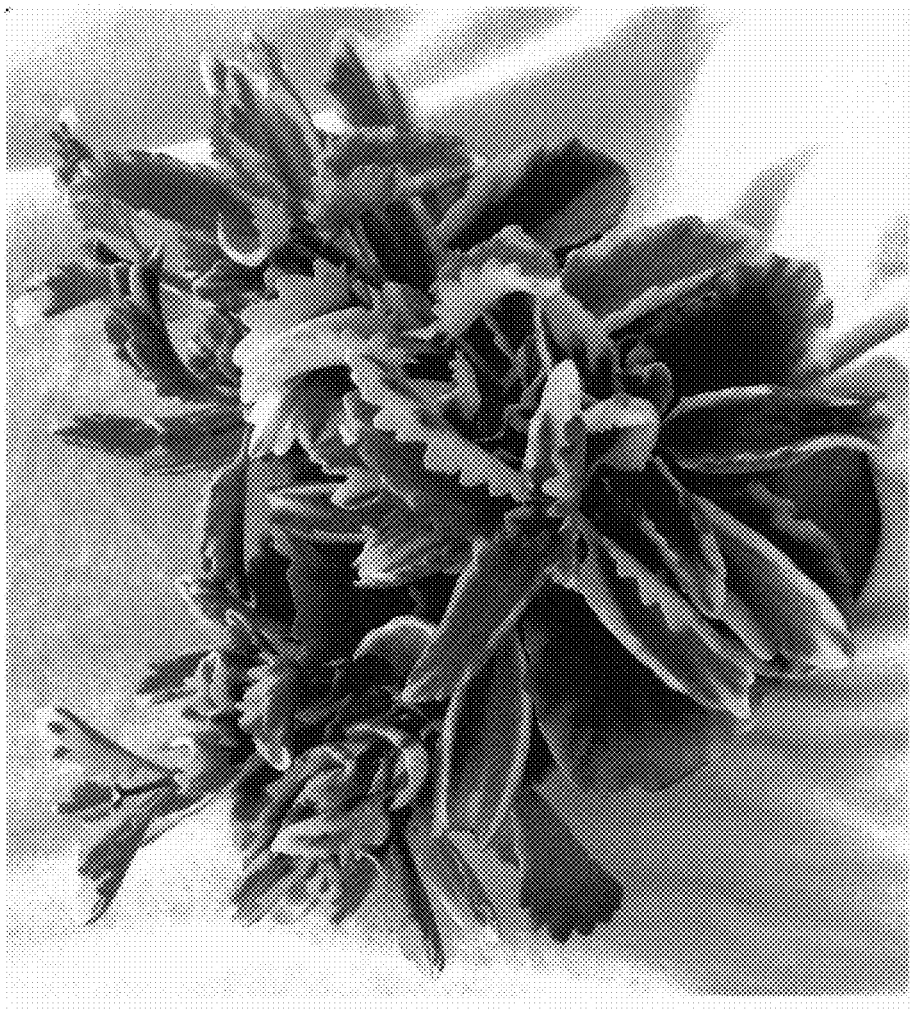

* * * * *